United States Patent [19]

Lovelock

[11] Patent Number: 4,780,284

[45] Date of Patent: Oct. 25, 1988

[54] GAS CHROMATOGRAPHY

[75] Inventor: James E. Lovelock, Cornwall, Great Britain

[73] Assignee: Hewlett-Packard Company, Palo Alto, Calif.

[21] Appl. No.: 831,790

[22] PCT Filed: Jun. 5, 1985

[86] PCT No.: PCT/GB85/00237

§ 371 Date: Mar. 27, 1986

§ 102(e) Date: Mar. 27, 1986

[87] PCT Pub. No.: WO85/05682

PCT Pub. Date: Dec. 19, 1985

[30] Foreign Application Priority Data

Jun. 5, 1984 [GB] United Kingdom ............... 8414311

[51] Int. Cl.$^4$ ........................................... G01N 23/00
[52] U.S. Cl. ................................. 422/83; 250/283; 250/306; 250/423 P; 422/54; 422/89; 436/35; 436/153
[58] Field of Search ................. 250/281–283, 250/288, 289, 293, 306, 307, 309, 423 P; 422/54, 89, 83; 436/153, 154, 35

[56] References Cited

U.S. PATENT DOCUMENTS

| 3,626,181 | 12/1971 | Wernlund | 250/282 |
| 4,028,617 | 6/1977 | Kamo et al. | 250/382 X |
| 4,063,156 | 12/1977 | Patterson | 250/386 X |

FOREIGN PATENT DOCUMENTS 989614 9/1941 United Kingdom .
1564499 4/1980 United Kingdom .

Primary Examiner—Michael S. Marcus
Attorney, Agent, or Firm—Donald N. Timbie

[57] ABSTRACT

Apparatus for detecting gas in a sample gas in a carrier gas stream and including a windowless ionization detector having a pulsed power supply which is switchable at a rate which provides a pulse period shorter that the transit time of ions to be detected to the collector electrode of an ionization chamber of the detector. Switching allows any signal due to ion detection to be separated from background noise due to other effects in the chamber.

6 Claims, 2 Drawing Sheets

GAS CHROMATOGRAPHY

This invention is concerned with gas chromatography, and is especially concerned with detectors for detecting low concentrations of a specific gas in gas samples in gas chromatography.

The photoionization detector is one type of detector which is used in this field and, typically, it is capable of detecting concentrations of about $10^{-4}$ to $10^{-10}$ of the gas to be traced. There are two versions of the photoionization detector, one of which, the "window-type" detector, is capable of operating at atmospheric pressure, and the other of which, the "windowless-type" detector, is designed to operate at low pressures, i.e., less than 50 Torr. It is the "windowless-type" of detector with which this invention is predominantly concerned.

The windowless-type photoionisation detector typically comprises a hollow vessel which may be a quartz tube having an outlet port for connection of a low pressure vacuum pump thereto, a gas source at one end of the tube for providing ultraviolet radiation, and an inlet for gas samples at the other end of the tube. Between the two ends of the quartz tube (glass or a suitable metal may also be used as the material of the tube), a collimator is provided for collimating the ultraviolet radiation directed along the tube towards the sample gas inlet. A cathode is provided at the gaseous source, typically in an inlet through which the source gas enters the quartz tube, and an anode is provided at the mouth of the sample gas inlet. An ion chamber defined by a metal cylinder encloses longitudinally the mouth of the sample gas inlet and is usually maintained at ground potential relative to the anode.

In the operation of the detector, the cylinder of the ion chamber collects the ions produced by the radiation acting upon the sample gas and is connected to monitoring and measuring equipment which translates the current due to the ions collected into a signal which provides an indication of the presence or absence of specific gases.

A drawback which has hindered the wider application of the windowless photoionization detector is the relatively high level of background current, which gives rise to noise in the received signal. The observed noise levels impose severe limitations upon the minimum detectable signal. The background current is caused by a number of different phenomena, namely (a) photoelectric emission from the electrodes and from other internal surfaces of the detector which are either directly or indirectly exposed to the ultraviolet radiation;

(b) ionizing collisions between metastable atoms or molecules and the surfaces of the electrodes or other internal surfaces of the detector;

(c) ions which are blown into the ion chamber from the ultraviolet radiation source.

All of these effects magnify the noise due to instability of the ultraviolet radiation source.

The present invention provides apparatus for detecting gas in a sample gas in a carrier gas stream, the apparatus comprising a windowless photoionization detector comprising a vessel having a cathode, a first inlet through which a source gas for providing ultraviolet radiation can be introduced, a second, sample gas/carrier gas inlet, a port to which vacuum pump means can be connected, and collector electrode means for collecting ions produced by ionization within the detector; and vacuum pump means for maintaining pressure within the photoionization detector between 0.1 Torr and 50 Torr; the apparatus being characterized by means for alternately switching a power supply to the cathode on and off at a rate providing a period which is longer than the transit time of ions to be detected within the photoionization detector.

In apparatus as set forth in the last preceding paragraph, it is preferred that means is provided for maintaining ambient temperature of the photoionization detector at a temperature in the range from 200° C. to 300° C.

In apparatus as set forth in either one of the last two immediately preceding paragraphs, it is preferred that the port is located at a position such that any metastables present in the detector can be pumped therefrom.

In apparatus as set forth in any one of the last three immediately preceding paragraphs, it is preferred that the cathode is a hollow cathode housed in a first chamber of the vessel, and the first inlet is connected to the first chamber, the second inlet being provided in a second, ionization chamber of the detector.

In apparatus as set forth in the last preceding paragraph, it is preferred that the first and second inlets are collinearly arranged, and means is provided for collineating ultraviolet radiation emitted from the source gas when the detector is in use to provide a beam which is collinear with the first and second inlets so that ultraviolet radiation can be directed at sample gas entering the second chamber of the detector through the second inlet.

Apparatus as set forth in any one of the last five immediately preceding paragraphs may further comprise amplifier means connected to the collector electrode means for amplifying a signal produced by the collection of ions thereon, gating means connected to the amplifier means for gating the output from the amplifier means to identify signal current due to said signal, low-pass filter means connected to the gating means, and means for monitoring and/or detecting the output of the low-pass filter means to provide an indication of detection of the presence of a selected gas in the sample gas.

Apparatus as set forth in the last preceding paragraph may further comprise delay means connected between the gating means and the alternate-switching means providing a feed-back loop for stabilizing the switching of the power supply.

The present invention further provides a photoionization detector comprising means whereby a collimated beam of ultraviolet radiation can be produced, a sample gas/carrier gas inlet positioned such that ultraviolet radiation can be directed at gas entering the detector through the inlet, a port to which vacuum pump means can be connected and collector electrode means for collecting ions produced by ionization within the detector, the inlet and the collector electrode being spaced apart within an ionization chamber and the detector being characterized in that means is provided for providing a uniform potential gradient between the inlet and the collector electrode.

In a detector as set forth in the last preceding paragraph, it is preferred that the means for providing a uniform potential gradient comprises a plurality of annular electrodes regularly arranged in coaxial relationship between the inlet and the collector electrode and electrically connected so as to control the rate of migration of ions towards the collector electrode.

In a detector as set forth in the last preceding paragraph, it is preferred that the annular electrodes are provided within a cylindrical chamber of the detector between the collector electrode and a further electrode provided adjacent the inlet.

In a detector as set forth in the last preceding paragraph but one, the means for providing a uniform potential gradient may alternatively comprise a ceramic tube having means connected thereto for causing a low current to flow along the tube.

The present invention further provides in or for a windowless photoionization detector, an ionization chamber comprising a first inlet through which ionizing radiation can enter the chamber and a second inlet through which sample gas can enter the chamber to be ionized by the ionizing radiation, and two spaced electrodes, one of which provides a collector electrode, the ionization chamber being characterized by a plurality of annular electrodes regularly arranged in coaxial relationship between the two spaced electrodes to provide a uniform electric field for controlling the rate of migration of ions towards the collector electrode.

The noise level of the ultraviolet radiation source can be reduced by using a hollow cathode or, alternatively, by using an inductively or capacitively coupled plasma for the generation of the ultraviolet radiation.

There now follows a detailed description which is to be read with reference to the accompanying drawings of two apparatuses according to the present invention; it is to be clearly understood that these apparatuses have been selected for description to illustrate the invention by way of example and not by way of limitation.

Figure 1:
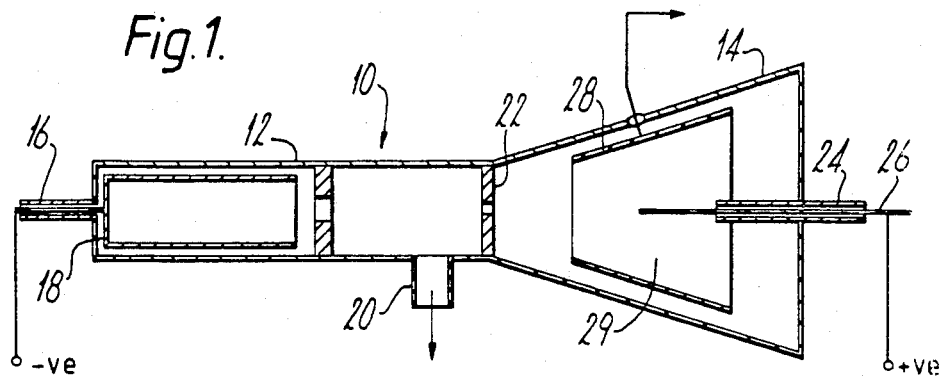
FIG. 1 is a diagrammatic view of a windowless photoionization detector.

In FIG. 1, the illustrated windowless photoionization detector comprises a vessel 10 made of glass or quartz and itself comprising a tubular portion 12 and a frusto-conical portion 14. The tubular portion 12 has an inlet 16 through which a source gas for providing ultraviolet radiation can be introduced into the vessel. Mounted within the tubular portion 12 is a hollow cathode 18 which is connected to a power supply (shown in FIG. 2) and produces a high intensity, stable discharge of radiation from the source gas. The tubular portion 12 also has an outlet port 20 which is connected to a vacuum pump (not shown) capable of maintaining a pressure of between 0.1 Torr and 50 Torr within the vessel 10.

Mounted at or adjacent the junction of the two portions of the vessel is a collimator 22 having an aperture aligned along the axis of the tubular portion of the vessel with the inlet 16. The frusto-conical portion 14 of the vessel 10 has an inlet 24 which is aligned with the collimator aperture and with the inlet 16. Within the inlet is provided an anode 26, made of platinum or nickel wire, which extends from the mouth of the inlet 24 into the frusto-conical portion 14. Surrounding the anode circumferentially is a collector electrode 28 also of frusto-conical shape and arranged to collect ionization current. The electrode 28 is maintained at ground potential, i.e., negative relative to the anode 26 so that an applied field exists between the two electrodes 26 and 28 which is sufficient to allow the ions to be collected but not so large as to cause field intensified ionization.

When the photoionization detector is in use, the source gas is supplied through the inlet 16. The most commonly used gases for providing ultraviolet radiation are helium, argon and hydrogen. A potential sufficient to provide the ultraviolet radiation is applied between the cathode 18 and the anode 26 by a power supply 30 (shown in FIG. 2) which is operable to interrupt the ultraviolet discharge, by, for example, modulating or pulsing the electrical energy supplied to it, for the reasons explained below.

Simultaneously with the period during which the ultraviolet discharge is maintained, intermittently, along the detector, sample gas, containing a gas to be detected, is introduced through the inlet 24 in a carrier stream of a gas which is substantially transparent to the ultraviolet radiation, for example nitrogen, air, steam or carbon dioxide. The sample gas may comprise any one of a number of inorganic gases and vapours including $CS_2$, NO, $NH_3$ and $H_2S$, as well as most organic vapours.

The ionizable constituents of the sample gas are ionized by the ultraviolet radiation as the sample gas exits from the inlet 24 and the ions move toward the collector electrode 28, where they are collected and generate a current which is applied as a signal to a power amplifier. The ultraviolet discharge also causes photoelectric emission from the electrodes and can cause like emission from other surfaces, e.g., the internal surfaces of the vessel; ions can also be blown from the UV source into the ion chamber 29. To a certain extent such emissions within the portion 12 of the vessel are restricted by the collimator aperture, but any effect within the portion 14 will cause charge to collect upon the surface of the electrode 28. In addition, rare gas atoms, such as can be introduced by using these gases as the ultraviolet source gases, can be readily excited to their metastable states by electron impact. Ionizing collisions occur between these metastable atoms, or between molecules of the carrier gas, and the anode and other surfaces, to produce ions which will also be collected on the electrode 28. If the discharge were continuous and uninterrupted, as in the prior art, each of these additional effects would produce background noise which when superimposed on the desired signal, i.e., the signal corresponding to the sample gas to be detected can mask the signal to such an extent as to seriously affect the detectivity of the detector apparatus.

Figure 2:
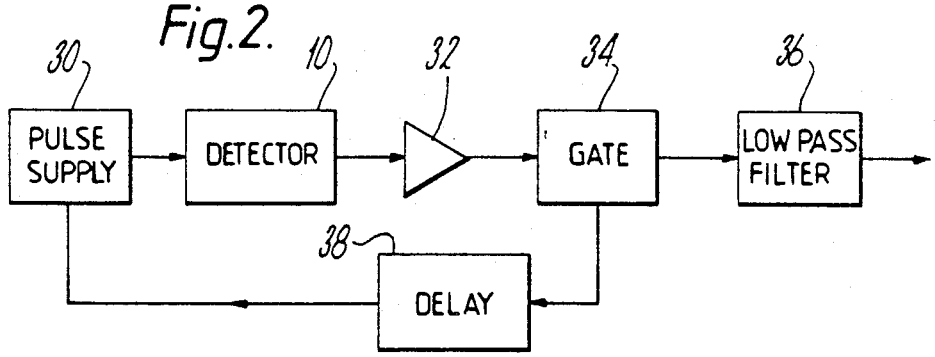
FIG. 2 is a block diagram of apparatus according to the present invention.
Figure 3:
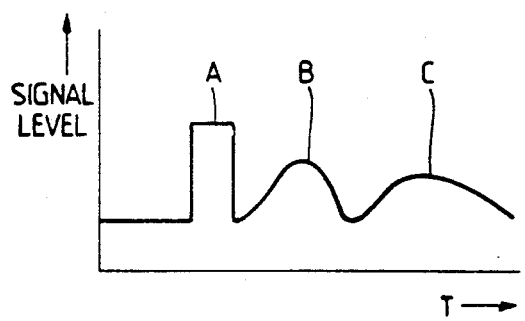
FIG. 3 is a graph illustrating signal strength and separation achieved by the present invention.

These undesirable effects can be overcome by an apparatus according to the invention such as that shown in FIG. 2. The feature of this apparatus is that it includes a power supply which operates the ultraviolet radiation source intermittently. By this simple expedient, advantage can be taken of the different migration rates of the various emissions and ions to provide for separation of the signals generated by each, as shown in FIG. 3. By "flashing" the ultraviolet source on, each of the above effects takes place. Photoelectron current is detected first due to the higher velocity of the electrons, whereas the signal corresponding to the current generated due to the metastables and molecules referred to above, or due to the ions from the ultraviolet radiation source appears much later. This may, depending upon the gases used, and the materials used for construction of the component parts of the detector, be due to the greater distance of the ultraviolet source 18 from the collector electrode 28 when compared with the distance travelled by the ions of the sample gas from the anode 26 to the electrode 28, and due also to the slower migration rate where the metastables or molecules are heavier than the ions to be detected.

If the pulsing rate is maintained so that each pulse period is longer than the transit time of the ions, for example one-tenth of a millisecond, separation of the effects can be obtained as shown in FIG. 3, where the signal due to the photoelectric current is indicated by the square wave portion A, the signal due to the gas which is to be detected is the intermediate peak B and the elongate peak is due to the signal resulting from the prolonged migration of the metastables or molecules, and secondary effects resulting therefrom.

Any effect due to the presence of metastables can be greatly reduced by raising the ambient temperature of the photoionization detector to temperatures in the range of 200° to 300°; metastables disappear very quickly at these higher temperatures. A further way of reducing the effect of the metastables is to locate the pump port 20 so that they can be pumped from the vessel 10.

In the circuit diagram of FIG. 2, an amplified output signal from the amplifier 32 is gated by a gating circuit 34 so that the signal current can be distinguished from that due to the other effects. The circuit has an output to a low pass filter 36 and hence to a monitor and/or recording means (not shown), and an output to a delay circuit 38 in a feed-back loop to the pulsed power supply 30 to control the pulsing rate thereof.

Inherent noise which is due directly to fluctuation in the ultraviolet radiation level can also seriously affect sensitivity of the apparatus and therefore the ability of an operator to detect peaks in the signal observed and so the presence of a gas. To minimize the effect of noise, the output from the source of ultraviolet radiation can be used to control the level of radiation by imposing a feed-back loop (not shown) upon the source to steady the output and then maintain it at a constant level. Then provided that the rate at which source gas is introduced into the detector, the radiation emitted by the gas can be maintained at a constant intensity together with any noise produced by the radiation.

Figure 4:
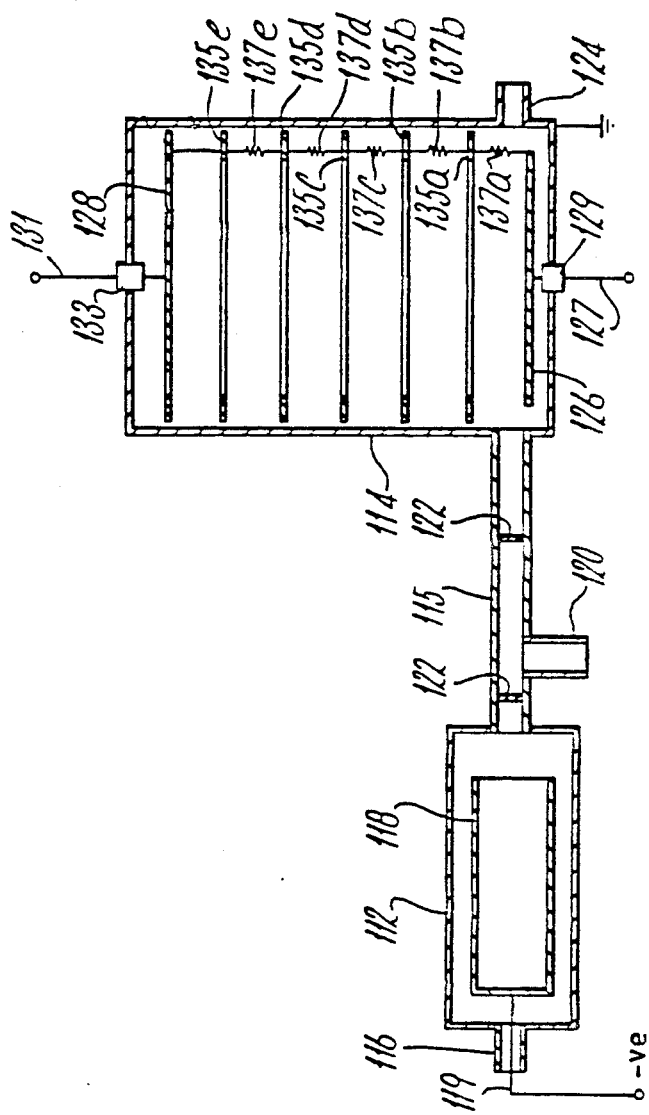
FIG. 4 is a diagrammatic view of a second windowless photoionization detector.

In FIG. 4 there is shown a second windowless photoionization detector which essentially comprises two chambers 112 and 114 which are connected by a hollow tube 115. The chamber 112 is cylindrical and is provided with a gas inlet 116 through which source gas for providing ultraviolet radiation can be introduced into the chamber 112, just as with the detector shown in FIG. 1. Mounted within the chamber 112 is a hollow canister-shaped cathode 118 connected by a conductor 119 to the negative terminal of a power supply (30 in FIG. 2).

The hollow tube 115 includes an outlet port 120 for connection of a vacuum pump thereto, and may be of a diameter such that the tube itself serves to collimate the ultraviolet radiation emanating from the cathode 118. Alternatively, collimators 122 can be mounted within the tube.

The chamber 114 has an inlet 124 which is aligned with the axis of the tube 115 and of the cathode 118. The chamber is in the form of an upright cylinder closed at both ends and having a circular, flat, plate-shaped electrode 126 mounted adjacent the base of the chamber and connected via a conductor 127 extending through an insulator 129 to a first terminal of a source of polarizing potential (not shown). A second electrode 128, similar to the electrode 126, is mounted at the top of the chamber 114, and is connected via a conductor 131 extending through an insulator 133 to a second terminal of the polarizing potential source.

Mounted within the chamber 114, which is maintained at ground potential, at regularly spaced intervals between the electrode 126 and the electrode 128 is a plurality of annular electrodes 135a–137e. These annular electrodes are serially connected between the electrode 126 and the walls of the chamber 114, electrode 137e being in the plane of the electrode 128, by appropriate resistors 137a–137e connected between adjacent electrodes. The electrodes 135a–135f maintain a controlled potential gradient and thus control the migration rate of ions between the electrodes 126 and 128. When the detector is in use the potential between the two electrodes 126 and 128 may be typically from 10 to 100 volts depending upon the gas which is to be ionized and the pressure which is to be maintained within the detector; the greater the pressure and the heavier the ions to be collected by the electrode, the greater will be the potential difference. The electrode 126 may be maintained at a potential which is positive or negative with respect to the collector electrode 128, depending upon the polarity of the ions to be collected. The field gradient up which the ions migrate can also be established by a slightly conducting ceramic tube down which a current flows. This avoids the plurality of conducting rings which are more expensive to construct.

When the detector is in use ultraviolet radiation is emitted by the source gas admitted through the inlet 116 due to the potential difference between the cathode 118, and the chamber 114, and the radiation is transmitted along the tube to ionize gas introduced through the sample gas inlet 124. The ions produced by the ionization of the sample gas migrate towards the collector electrode 128 as is explained in more detail with reference to FIG. 1. It is sometimes advantageous to have a uniform flow of gas travelling counter to the ions in the drift tube.

I claim:

1. Apparatus for detecting gas contained in a stream of carrier gas comprising
   a hollow closed vessel,
   means defining a first inlet in said vessel through which source gas may be introduced into a given portion of the space in said vessel,
   means including electrode means for producing pulses of ultraviolet light at spaced intervals by subjecting said given portion of the space in said vessel into which said source gas may flow to a pulsed electrical field,
   means defining a second inlet through which carrier gas including a gas to be detected may be introduced into said vessel,
   means defining a port through which gas may flow out of said vessel,
   collimating means mounted within said vessel for directing ultraviolet light to said second inlet in the form of a beam,
   a pair of electrodes mounted in said vessel in such location that carrier gas entering said vessel via said second inlet passes between them, and
   an output circuit coupled to said pair of electrodes for producing current only during periods of time following each pulse of ultraviolet light during which ions produced from a gas being detected arrive at one said pair of electrodes.

2. Apparatus as set forth in claim 1 wherein said electrode means includes a hollow cathode.

3. Apparatus as set forth in claim 1 wherein said port is located such that metastables produced during the production of ultraviolet light by said electrical field can be pumped by a pump means from said vessel.

4. Apparatus as set forth in claim 3 wherein means are provided for applying a steady direct current voltage between the electrodes of said pair, and an output circuit including a gate circuit is coupled between the electrodes of said pair.

5. Apparatus as set forth in claim 1 wherein said output circuit includes means for placing a direct current voltage between said pair of electrodes, a normally closed gating means and control means for opening said gating means during said period.

6. Apparatus as set forth in claim 5 wherein feedback means is coupled between said control means and said means for producing pulses of ultraviolet light for stabilizing the latter.

* * * * *